(12) United States Patent
Braun et al.

(10) Patent No.: US 7,834,085 B2
(45) Date of Patent: Nov. 16, 2010

(54) COMPOSITION AND METHOD FOR PREPARING NOVEL CATIONIC THICKNERS

(75) Inventors: Olivier Braun, Naves (FR); Paul Mallo, Croissy-sur-Seine (FR); Herve Rolland, Castres (FR)

(73) Assignee: Societe d'Exploitation de Produits pour les Industries Chimiques SEPPIC, Paris (FR)

(*) Notice: Subject to any disclaimer, the term of this patent is extended or adjusted under 35 U.S.C. 154(b) by 0 days.

(21) Appl. No.: 12/716,081

(22) Filed: Mar. 2, 2010

(65) Prior Publication Data

US 2010/0160535 A1 Jun. 24, 2010

Related U.S. Application Data

(62) Division of application No. 11/321,399, filed on Dec. 29, 2005, which is a division of application No. 10/777,848, filed on Feb. 12, 2004, now Pat. No. 7,015,279.

(30) Foreign Application Priority Data

Feb. 13, 2003 (FR) .................................. 0301723

(51) Int. Cl.
  *C08F 2/32* (2006.01)
(52) U.S. Cl. ................. 524/801; 524/804; 524/815; 524/829; 524/831
(58) Field of Classification Search ........... 524/801, 524/804, 815, 829, 831
See application file for complete search history.

(56) References Cited

U.S. PATENT DOCUMENTS

| 4,806,345 | A | 2/1989 | Bhattacharyya |
| 4,981,936 | A | 1/1991 | Good |
| 5,100,660 | A | 3/1992 | Hawe et al. |
| 5,238,992 | A | 8/1993 | Outubuddin |
| 6,136,305 | A | 10/2000 | Michel-Lecocu et al. |
| 6,197,287 | B1 * | 3/2001 | Mallo et al. ............ 424/70.16 |
| 6,346,239 | B1 | 2/2002 | Mallo et al. |
| 6,375,959 | B1 | 4/2002 | Mallo et al. |
| 6,454,003 | B1 | 9/2002 | Chang et al. |
| 6,531,561 | B2 | 3/2003 | Candau et al. |
| 6,831,107 | B2 | 12/2004 | Dederen et al. |
| 7,378,479 | B2 | 5/2008 | Tamareselvy et al. |
| 2002/0032243 | A1 | 3/2002 | Tabacchi et al. |
| 2004/0030034 | A1 | 2/2004 | Chang et al. |

FOREIGN PATENT DOCUMENTS

| EP | 0 161 038 | 11/1985 |
| EP | 0 900 786 A1 | 3/1999 |
| FR | 2 721 5111 | 12/1995 |
| FR | 2 773 805 | 7/1999 |
| FR | 2 774 688 | 8/1999 |
| FR | 2 774 996 | 8/1999 |
| FR | 2 782 086 | 2/2000 |
| FR | 2 785 801 | 5/2000 |
| FR | 2 786 493 | 6/2000 |
| FR | 2 787 457 | 6/2000 |
| FR | 2 789 395 | 8/2000 |
| FR | 2 794 034 | 12/2000 |
| FR | 2 794 124 | 12/2000 |
| FR | 2 808 446 | 11/2001 |
| FR | 2 808 447 | 11/2001 |
| FR | 2 810 883 | 1/2002 |
| WO | WO 97 22640 A | 6/1997 |
| WO | WO 00 32639 | 6/2000 |

OTHER PUBLICATIONS

French Search Report for FR 0301723.
Chang et al. US 2004/0030034 A 1, Feb. 12, 2004.
Loffler et al. US 2004/0141937 A1, Jul. 22, 2004.

* cited by examiner

*Primary Examiner*—Bernard Lipman
(74) *Attorney, Agent, or Firm*—Young & Thompson

(57) ABSTRACT

A self-reversible invert latex having a crosslinked cationic polyelectrolyte, formed by the copolymerization of at least one cationic monomer with at least one neutral monomer and at least one nonionic surfactant monomer.

3 Claims, No Drawings

COMPOSITION AND METHOD FOR PREPARING NOVEL CATIONIC THICKNERS

This application is a division of application Ser. No. 11/321,399 filed on Dec. 29, 2005, which is a division of application Ser. No. 10/777,848 filed on Feb. 12, 2004, now U.S. Pat. No. 7,015,279, which claimed priority to French application no. 0301723, filed on Feb. 13, 2003. The entire contents of each of the above-identified applications are hereby incorporated by reference.

The subject of the invention is novel polymers, their method of preparation and their use as thickening and/or emulsifying agent.

BACKGROUND OF THE INVENTION

The thickening of aqueous phases is generally carried out by incorporating therein hydrophilic polymers of all sorts, whether they are synthetic or of natural origin.

Among the polymers of natural origin, xanthan or guar gums are fairly widely used. They however have the conventional disadvantages of natural products, namely a fluctuating quality and price.

Among the hydrophilic synthetic thickeners most widely used are polymers in the form of self-reversible invert latexes or powders. They are used in a wide pH range and are often well tolerated by humans. Such compositions are described for example in French patents and patent applications published under the numbers 2721511, 2773805, 2774688, 2774996, 2782086, 2785801, 2786493, 2787457, 2789395, 2794034, 2794124, 2808446, 2808447 and 2810883.

These polymers are anionic and are essentially intended to thicken and/or emulsify cosmetic, dermo-pharmaceutical or pharmaceutical topical formulations which contain numerous constituents such as oils, nonionic or anionic surfactants, inorganic salts and/or weak acids.

Some formulations, in particular those intended for hair care, also contain cationic surfactants and/or cationic conditioning polymers. In this particular case, thickeners consisting of anionic polymers are not recommended because of electrostatic interactions between the positive and negative charges which cause precipitation of the polymer, and cationic thickening polymers such as those described in American patents published under the numbers U.S. Pat. No. 4,806,345 and U.S. Pat. No. 5,100,660 are preferably used.

Although the latter behave satisfactorily in an acidic medium and are compatible with cationic surfactants, they nevertheless lose their thickening power in formulations high in electrolytes.

Accordingly, the applicant focussed on developing novel thickeners of a cationic nature, which are compatible with cationic surfactants while preserving their thickening power in media high in electrolytes.

SUMMARY OF THE INVENTION

The present invention relates to novel linear or crosslinked cationic polyelectrolyte composition, wherein said composition comprises copolymerization of at least one cationic monomer with at least one neutral monomer and at least one nonionic surfactant monomer.

DETAILED DESCRIPTION OF THE INVENTION

According to a first aspect, the subject of the invention is a linear or crosslinked cationic poly-electrolyte, characterized in that it is obtained by copolymerization of at least one cationic monomer with at least one neutral monomer and at least one nonionic surfactant monomer.

The expression crosslinked polyelectrolyte denotes a nonlinear polyelectrolyte which exists in the form of a three-dimensional network which is insoluble in water, but which is capable of swelling in water and therefore leading to the production of a chemical gel.

The expression copolymerization means, in the context of the present invention, that the polymerization reaction uses at least three different monomers. It can however involve more than three different monomers.

The expression neutral monomer denotes monomers not containing any strong or weak acid functional group or any positively charged group. They are more particularly chosen from acrylamide, methacrylamide, vinylpyrrolidone, diacetoneacrylamide, dimethylacryl-amide, (2-hydroxyethyl) acrylate, (2,3-dihydroxypropyl)acrylate, (2-hydroxyethyl) methacrylate, (2,3-dihydroxy-propyl)methacrylate or an ethoxylated derivative having a molecular weight of between 400 and 1000, of each of these esters.

The expression cationic monomers denotes more particularly monomers containing a quaternary ammonium functional group. They are more particularly chosen from 2,N,N,N-tetramethyl-2-[(1-oxo-2-propenyl)amino]propan-ammonium chloride (AMPTAC), 2,N,N-trimethyl-2-[(1-oxo-2-propenyl)amino]propanammonium chloride, N,N,N-tri-methyl-3-[(1-oxo-2-propenyl)amino]propanammonium chloride (APTAC), diallyldimethylammonium chloride (DADMAC), N,N,N-trimethyl-2-[(1-oxo-2-propenyl)]ethanammonium chloride, N,N,N-trimethyl-2-[(1-oxo-2-methyl-2-propenyl)]-ethanammonium chloride, N-[2-(dimethylamino)-1,1-dimeth-yl]acrylamide, N-[2-(methylamino)-1,1-dimethyl]acryl-amide, 2-(dimethylamino)ethyl acrylate, 2-(dimethyl-amino)ethyl methacrylate or N-[3-(dimethylamino)propyl]-acrylamide.

The expression nonionic surfactant monomer denotes more particularly the polyalkoxylated derivatives of esters of monomers containing a weak acid functional group with fatty alcohols. Such compounds are represented either by general formula (I):

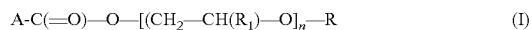

$$A\text{-}C(=O)\text{---}O\text{---}[(CH_2\text{---}CH(R_1))\text{---}O]_n\text{---}R \qquad (I)$$

or alternatively by general formula (I'):

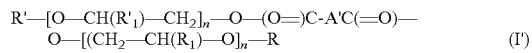

$$R'\text{---}[O\text{---}CH(R'_1)\text{---}CH_2]_{n'}\text{---}O\text{---}(O=)C\text{-}A'C(=O)\text{---}$$
$$O\text{---}[(CH_2\text{---}CH(R_1))\text{---}O]_n\text{---}R \qquad (I')$$

in which formulae (I) and (I'):

n and n' represent, independently of each other, a number between 1 and 50;

A represents an unsaturated aliphatic monovalent radical comprising from 2 to 6 carbon atoms, A' represents an unsaturated aliphatic divalent radical comprising from 2 to 6 carbon atoms, $R_1$ and $R'_1$ represent, independently of each other, a hydrogen atom, a methyl radical or an ethyl radical; and R and R' represent, independently of each other, a saturated or unsaturated, linear or branched, aliphatic hydrocarbon radical comprising from 8 to 30 carbon atoms.

In formulae (I) and (I'), as defined above, the divalent radicals:

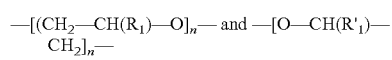

$$-[(CH_2-CH(R_1)-O]_n- \text{ and } -[O-CH(R'_1)-CH_2]_{n'}-$$

represent, independently of each other:

either chains composed solely of ethoxyl groups ($R_1$=H; n>0), or chains composed solely of propoxyl groups ($R_1=CH_3$; n>0), or chains composed solely of butoxyl groups ($R_1=C_2H_5$; n>0), or chains composed of at least two different groups chosen from ethoxyl, propoxyl and/or butoxyl groups.

When these chains are composed of different groups, they are distributed right along this chain, in a block or randomly.

The expression unsaturated aliphatic monovalent radical comprising from 2 to 6 carbon atoms denotes more particularly for A, the vinyl radical ($CH_2=CH-$) or the 2-propenyl radical [$CH_2=C(CH_3)-$].

The expression unsaturated aliphatic divalent radical comprising from 2 to 6 carbon atoms denotes more particularly for A', the 1,2-ethenediyl radical ($-CH=CH-$) or the 2-propene-1,2-diyl radical [$-CH_2-C(=CH_2)-$].

The expression saturated or unsaturated, linear aliphatic hydrocarbon radical comprising from 8 to 30 carbon atoms denotes more particularly for R and R', the radicals derived from linear primary alcohols such as for example those derived from octyl, pelargonic, decyl, undecyl, undecenyl, lauryl, tridecyl, myristyl, pentadecyl, cetyl, heptadecyl, stearyl, oleyl, linoleyl, nonadecyl, arachidyl, behenyl, erucyl or 1-triacontanoic alcohols. They are in this case octyl, nonyl, decyl, undecyl, 10-undecenyl, dodecyl, tridecyl, tetradecyl, pentadecyl, hexadecyl, heptadecyl, octa-decyl, 9-octadecenyl, 10,12-octadecadienyl, 13-docosenyl or triacontanyl radicals.

The expression saturated or unsaturated, branched aliphatic hydrocarbon radical comprising from 8 to 30 carbon atoms denotes more particularly for R and R', either the radicals derived from Guerbet alcohols, which are branched 1-alkanols corresponding to general formula:

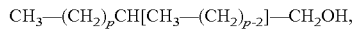

in which p represents an integer between 2 and 14, such as for example the 2-ethylhexyl, 2-propylheptyl, 2-butyloctyl, 2-pentylnonyl, 2-hexyldecyl or 2-octyl-dodecyl radicals;

or the radicals derived from isoalkanols corresponding to general formula:

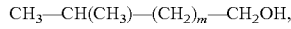

in which m represents an integer between 2 and 26, such as for example the 4-methylpentyl, 5-methylhexyl, 6-methylheptyl, 15-methylpentadecyl or 16-methylhepta-decyl radicals;

or the 2-hexyloctyl, 2-octyldecyl or 2-hexyl-dodecyl radicals.

The subject of the invention is more particularly a cationic polyelectrolyte as defined above, characterized in that the nonionic surfactant monomer is chosen from the compounds of formula (I) or the compounds of formula (I') as defined above, in which:

R and R' represent, independently of each other, a saturated or unsaturated, linear or branched, aliphatic hydrocarbon radical comprising from 8 to 18 carbon atoms, $R_1$ and $R'_1$ each represent a hydrogen atom, and n and n' represent, independently of each other, a number between 1 and 10.

The subject of the invention is more particularly a cationic polyelectrolyte as defined above, characterized in that:

from 5% to 35% of the monomeric units which it comprises is a cationic monomer, from 55% to 95% of the monomeric units which it comprises is a neutral monomer, and from 0.1% to 5% of the monomeric units which it comprises is a surfactant monomer.

According to another particular aspect of the present invention, its subject is a cationic poly-electrolyte as defined above, characterized in that it is obtained by copolymerization of at least one cationic monomer with at least one neutral monomer, at least one nonionic surfactant monomer and a non-zero proportion of N-[2-hydroxy-1,1-bis(hydroxymethyl)ethyl]-propenamide.

N-[2-Hydroxy-1,1-bis(hydroxymethyl)ethyl]propenamide, also called tris(hydroxymethyl)acrylamidomethane or THAM:

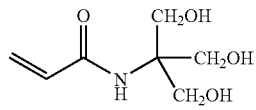

is described in European patent application published under the number EP 0 900 786.

When the polyelectrolyte which is the subject of the present invention contains a non-zero proportion of THAM monomer, from 5% to 35% of the monomeric units which it comprises is a cationic monomer, from 35% to 91% of the monomeric units which it comprises is a neutral monomer, from 0.1% to 5% of the monomeric units which it comprises is a nonionic surfactant monomer, and from 3% to 20% of the monomeric units which it comprises is the THAM monomer.

According to another particular aspect of the present invention, the polyelectrolyte as defined above is not crosslinked.

According to another particular aspect of the present invention, the polyelectrolyte as defined above is crosslinked. In the latter case, the crosslinking agent is chosen in particular from diethylenic or polyethylenic compounds, and most particularly from diallyloxyacetic acid or one of the salts and in particular its sodium salt, triallylamine, trimethylol propanetriacrylate, ethylene glycol dimethacrylate, diethylene glycol diacrylate, diallylurea or methylene bis(acrylamide).

The crosslinking agent is then generally used in the molar proportion, expressed relative to the monomers used, of 0.005% to 1%, in particular 0.01% to 0.2%, and more particularly 0.01% to 0.1%.

According to a second aspect of the present invention, its subject is a composition comprising an oily phase, an aqueous phase, at least one water-in-oil (W/O) type emulsifying agent, at least one oil-in-water (O/W) type emulsifying agent, in the form of a self-reversible invert latex comprising from 20% to 70% by weight, preferably from 25% to 40% by weight, of a cationic polyelectrolyte as defined above.

The self-reversible invert latex according to the invention generally contains from 2.5% to 15% by weight, and preferably from 4% to 9% by weight, of emulsifying agents, of which from 20% to 50%, in particular from 25% to 40% of the total weight of the emulsifying agents present are of the water-in-oil (W/O) type and in which from 80% to 50%, in particular from 75% to 60%, of the total weight of the emulsifying agents are of the oil-in-water (O/W) type.

In the self-reversible invert latex as defined above, the oily phase generally represents from 15% to 50%, preferably from 20% to 25%, of its total weight.

The self-reversible invert latex also contains between 5% and 60% by weight of water and more particularly between 20% and 50% by weight of water.

The self-reversible invert latex according to the invention may also contain various additives such as complexing agents or chain-regulating agents.

The expression "water-in-oil type emulsifying agent" denotes emulsifying agents possessing a sufficiently low HLB value to form water-in-oil emulsions, such as the surfactant polymers marketed under the name HYPERMER™ such as HYPERMER™ B246, HYPERMER™ B41 or HYPERMER™ 2296 or such as sorbitan esters, such as the sorbitan monooleate marketed by the company SEPPIC under the name MONTANE™ 80, the sorbitan isostearate marketed by SEPPIC under the name MONTANE™ or the sorbitan sesquioleate marketed by SEPPIC under the name MONTANE™ 83. In the case of a mixture of water-in-oil type emulsifying agents, the HLB value to be taken into consideration is that of the said mixture.

The expression "oil-in-water type emulsifying agent" denotes emulsifying agents possessing a sufficiently high HLB value to give oil-in-water emulsions such as for example the ethoxylated sorbitan esters such as the ethoxylated sorbitan oleate containing 20 moles of ethylene oxide, ethoxylated castor oil containing 40 moles of ethylene oxide, ethoxylated sorbitan laurate containing 20 moles of ethylene oxide which are marketed by the company SEPPIC under the names MONTANOX™ 80, SIMULSOL™ OL 50 and MONTANOX™ 20, respectively, the ethoxylated lauryl alcohol containing 7 moles of ethylene oxide marketed by the company SEPPIC under the name SIMULSOL™ P7, the decaethoxylated oleocetyl alcohol of ethylene marketed by the company SEPPIC under the name SIMULSOL™ OC 710 or the polyethoxylated sorbitan hexaoleates marketed by the company ATLAS Chemical Industries under the names G-1086 and G-1096, ethoxylated nonylphenols.

The oily phase of the self-reversible invert latex described above consists:

either of a commercially available mineral oil containing saturated hydrocarbons of the paraffin, isoparaffin and cycloparaffin type, having at room temperature a density between 0.7 and 0.9 and a boiling point greater than 180° C., such as for example ISOPAR™ M or ISOPAR™ L, EXXOL™ D 100 S marketed by EXXON or the white mineral oils in conformity with the FDA regulations 21 CFR 172,878 and FR 178,3620(a), such as MARCOL™ 52 or MARCOL™ 82, also marketed by EXXON;

or of the hydrogenated polyisobutene marketed in France by the company Ets B. Rossow and Co under the name PARLEAM-POLYSYNLANE™ and cited in Michel and Irene Ash; Thesaurus of Chemical products, Chemise Publicité Cos, Ince. 1986 Volume 1, page 211 (ISBN 0 7131 3603 0);

or of the isohexadecane identified in Chemical Abstracts by the number RN=93685-80-4 and which is a mixture of $C_{12}$, $C_{16}$ and $C_{20}$ isoparaffins containing at least 97% of $C_{16}$ isoparaffins, of which the principal constituent is 2,2,4,4,6,8,8-heptamethylnonane (RN=4390-04-9), marketed in France by the company Bayer;

or of the isododecane marketed in France by the company Bayer;

or of the squalane which is identified in Chemical Abstracts by the number RN=111-01-3 and which is a mixture of hydrocarbons containing more than 80% by weight of 2,6,10,15,19,23-hexamethyltetracosane. It is marketed in France by the company SOPHIM, under the name PHYTOSQUALANE™;

or of the fatty acid esters of formula (II):

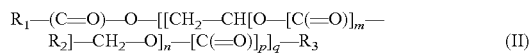
(II)

in which $R_1$ represents a linear or branched, saturated or unsaturated hydrocarbon chain containing from 7 to 30 carbon atoms, $R_2$ represents, independently of $R_1$, a hydrogen atom, a linear or branched, saturated or unsaturated hydrocarbon chain containing from 7 to 30 carbon atoms, $R_3$ represents, independently of $R_1$ or of $R_2$, a hydrogen atom or a linear or branched, saturated or unsaturated hydrocarbon chain containing from 1 to 30 carbon atoms, m, n, p and q are, independently of each other, equal to 0 or 1, it being understood that when $R_3$ represents a hydrogen atom, q is different from 0. As compounds of formula (II), there are more particularly the compounds of formula (IIa):

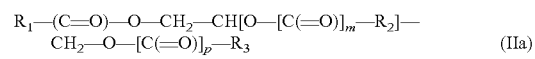
(IIa)

corresponding to formula (II) as defined above, in which q and n are equal to 1, or a mixture of compounds of formulae (IIa); in this case, they are, preferably, either a compound of formula (IIa$_1$):

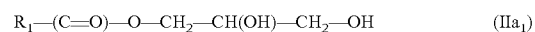
(IIa$_1$)

corresponding to formula (IIa) as defined above, in which m and p are equal to 0 and $R_2$ and $R_3$ represent a hydrogen atom, or a compound of formula (IIa$_2$):

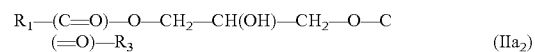
(IIa$_2$)

corresponding to formula (IIa) as defined above in which p is equal to 1, m is equal to 0 and $R_2$ represents a hydrogen atom, or a compound of formula (IIa$_3$)

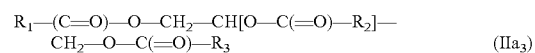
(IIa$_3$)

corresponding to formula (IIa) as defined above in which m and p are equal to 1, or a mixture of compounds of formulae (IIa$_1$), (IIa$_2$) and/or (IIa$_3$).

As examples of compounds of formulae (IIa$_1$), (IIa$_2$) or (IIa$_3$), there are for example triglycerides of fatty acids or of mixtures of fatty acids such as the mixture of fatty acid triglycerides containing from 6 to 10 carbon atoms, marketed under the name SOFTENOL™ 3819, the mixture of fatty acid triglycerides containing from 8 to 10 carbon atoms, marketed under the name SOFTENOL™ 3108, the mixture of fatty acid triglycerides containing from 8 to 18 carbon atoms, marketed under the name SOFTENOL™ 3178, the mixture of fatty acid triglycerides containing from 12 to 18 carbon atoms, marketed under the name SOFTENOL™ 3100, the mixture of fatty acid triglycerides containing 7 carbon atoms, marketed under the name SOFTENOL™ 3107, the mixture of fatty acid triglycerides containing 14 carbon atoms, marketed under the name SOFTENOL™ 3114 or the mixture of fatty acid triglycerides containing 18 carbon atoms, marketed under the name SOFTENOL™ 3118, glyceryl dilaurate, glyceryl dioleate, glyceryl iso-stearate, glyceryl distearate, glyceryl monolaurate, glyceryl monooleate, glyceryl monoisostearate, glyceryl monostearate or a mixture of these compounds.

According to a third aspect of the present invention, its subject is also a method for preparing a self-reversible invert latex as defined above, characterized in that:

a) an aqueous solution containing the monomers and the optional additives is emulsified in an oily phase in the presence of one or more water-in-oil type emulsifying agents and nonionic surfactant monomer, b) the polymerization reaction is initiated by introducing into the emulsion formed in a) a free radical initiator and optionally a coinitiator and then it is allowed to progress, c) when the polymerization reaction is complete, one or more oil-in-water type emulsifying agents are introduced at a temperature of less than 50° C.

According to one variant of this method the reaction medium derived from step b) is concentrated by distillation, before carrying out step c).

According to a preferred embodiment of the method as defined above, the polymerization reaction is initiated by an oxidation-reduction pair generating hydrogen sulphite ions ($HSO_3^-$), such as the cumene hydroperoxide-sodium metabisulphite ($Na_2S_2O_5$) pair or the cumene hydroperoxide-thionyl chloride ($SOCl_2$) pair at a temperature of less than or equal to 10° C., if desired accompanied by a polymerization coinitiator such as for example azobis(isobutyronitrile), dilauryl peroxide or sodium persulphate and then carried out either almost adiabatically until a temperature greater than or equal to 50° C. is obtained, or by controlling the temperature.

The polyelectrolyte as defined above may be isolated from the preceding self-reversible invert latex by various methods known to persons skilled in the art, such as the precipitation technique which consists in pouring the latex into a large excess of a solvent such as acetone, isopropanol or ethanol, or such as the spray-drying technique which is described in the international publication WO 00/01757 or by azeotropic dehydration.

According to a variant of the methods of preparation as defined above, the polyelectrolyte which is the subject of the present invention is isolated from the self-reversible invert latex.

The polyelectrolyte or the self-reversible invert latex which are the subject of the present invention may be used for example as a thickener for cosmetic or pharmaceutical compositions, as a thickener for printing pastes for the textile industry, as thickeners for industrial or household detergents, as additives for the petroleum industry, as a rheology modifier for drilling mud.

By virtue of its cationic character, the poly-electrolyte which is the subject of the present invention, and the self-reversible invert latexes containing it, are advantageously used as thickeners and/or as emulsifiers in cosmetic or pharmaceutical compositions intended for hair care and/or conditioning.

Such compositions are usually provided in the form of emulsion or microemulsion shampoos and in particular in the case of vaporizable emulsion conditioners.

Accordingly, according to a final aspect, the subject of the invention is a cosmetic or pharmaceutical composition, characterized in that it contains, as emulsifying and/or thickening agent, an effective quantity either of the cationic polyelectrolyte as defined above, or of the self-reversible invert latex containing it.

The cationic polyelectrolytes or the self-reversible invert latexes may be formulated in cosmetic, dermopharmaceutical or pharmaceutical formulas such as mousses, gels, lotions, sprays, shampoos, conditioners, lotions for the hands and the body, sunscreens, and more generally in care products.

The following examples illustrate the present invention without however limiting it.

A—EXAMPLES OF PREPARATION OF A SELF-REVERSIBLE INVERT LATEX CONTAINING POLYELECTROLYTES ACCORDING TO THE INVENTION

Example 1

Self-Reversible Invert Latex of the Copolymer: AM/APTAC/LA(4EO) (84.7/14.9/0.4) Crosslinked with MBA The following are loaded into a beaker, with stirring:
164.4 g of deionized water,
362.1 g of a commercial solution containing 50% of acrylamide (AM),
123.9 g of a commercial solution containing 75% of acrylamidopropyltrimethylammonium chloride (APTAC)
0.070 g of methylene bisacrylamide (MBA),
0.45 g of a commercial aqueous solution containing 40% of the sodium salt of diethylene-triaminepentaacetic acid.
An oily phase is prepared by successively mixing:
259 g of isohexadecane,
20 g of sorbitan isostearate (MONTANE™ 70),
5 g of HYPERMER™ 2296 (Uniquema),
5 g of tetraethoxylated lauryl acrylate [LA(4EO)],
0.1 g of azobis(isobutyronitrile) (AIBN).

The aqueous phase is gradually incorporated into the organic phase and then subjected to vigorous mechanical stirring by means of an ULTRA-TURRAX™ type turbine mixer in order to form an invert emulsion (water/oil).

The emulsion is then cooled to about 10° C. and placed under nitrogen bubbling for about 60 minutes in order to remove oxygen therefrom. The polymerization is then initiated by incorporating therein 10 cm$^3$ of a solution of cumene hydroperoxide at 0.68% by weight in isohexadecane. After homogenization of the medium, 25 g of an aqueous sodium metabisulphite solution at 0.1% by weight are added while allowing the temperature of the mixture to rise to the final polymerization temperature and then leaving the mixture for 90 minutes. The whole is then cooled to about 35° C., and then 40 g of ethoxylated lauryl alcohol at 7 moles (SIMULSOL™ P7) are added. The desired self-reversible invert latex is obtained.

Analysis

Polyelectrolyte content: about 27.5% by weight
Measurement of Viscosity

Viscosity of an aqueous solution containing 3% by weight of the self-reversible invert latex (Brookfield RVT, No. 6 rotor; speed: 5 revolutions per minute); $\eta$=45 000 mPa·s Viscosity of an aqueous solution containing 3% by weight of the self-reversible invert latex and containing 1‰ of sodium chloride (Brookfield RVT, No. 3 rotor; speed: 5 revolutions per minute); $\eta$=1 280 mPa·s.

Example 2

Self-Reversible Invert Latex of the Copolymer: Noncrosslinked AM/APTAC/THAM/LA(4EO) (77.7/14.9/7.0/0.4)

The following are loaded into a beaker, with stirring:
157.6 g of deionized water, 332.3 g of a commercial solution containing 50% of acrylamide (AM),
123.9 g of a commercial solution containing 75% of acrylamidopropyltrimethylammonium chloride (APTAC)
36.8 g of tris(hydroxymethyl)acrylamidomethane (THAM),
0.45 g of a commercial aqueous solution containing 40% of the sodium salt of diethylene-triaminepentaacetic acid.
An oily phase is prepared by successively mixing:
259 g of isohexadecane,
20 g of sorbitan isostearate (MONTANE™ 70),
5 g of HYPERMER™ 2296 (Uniquema),
5 g of tetraethoxylated lauryl acrylate [LA(4EO)],
0.1 g of azobis(isobutyronitrile) (AIBN).

The procedure is then carried out according to a procedure identical to that of Example 1 and the desired self-reversible invert latex is obtained.

Analysis

Polyelectrolyte content: about 29.7% by weight

Measurement of Viscosity

Viscosity of an aqueous solution containing 3% by weight of the self-reversible invert latex (Brookfield RVT, No. 6 rotor; speed: 5 revolutions per minute); $\eta$=48 200 mPa·s Viscosity of an aqueous solution containing 3% by weight of the self-reversible invert latex and containing 1‰ of sodium chloride (Brookfield RVT, No. 3 rotor; speed: 5 revolutions per minute); $\eta$=1 760 mPa·s.

Example 3

Self-Reversible Invert Latex of the Copolymer: Noncrosslinked AM/APTAC/THAM/LA(4EO) (72.7/19.9/7.0/0.4)

The following are loaded into a beaker, with stirring:
137.5 g of deionized water,
311 g of a commercial solution containing 50% of acrylamide (AM),
165.2 g of a commercial solution containing 75% by weight of acrylamidopropyltrimethyl-ammonium chloride (APTAC)
36.8 g of tris(hydroxymethyl)acrylamidomethane (THAM),
0.45 g of a commercial aqueous solution containing 40% of the sodium salt of diethylene-triaminepentaacetic acid.
An oily phase is prepared by successively mixing:
259 g of isohexadecane,
20 g of sorbitan isostearate (MONTANE™ 70),
5 g of HYPERMER™ 2296 (Uniquema),
5 g of tetraethoxylated lauryl acrylate [LA(4EO)],
0.1 g of azobis(isobutyronitrile) (AIBN).

The procedure is then carried out according to a procedure identical to that of Example 1 and the desired self-reversible invert latex is obtained.

Measurement of Viscosity

Viscosity of an aqueous solution containing 3% by weight of the self-reversible invert latex (Brookfield RVT, No. 6 rotor; speed: 5 revolutions per minute); $\eta$=84 000 mPa·s Viscosity of an aqueous solution containing 3% by weight of the self-reversible invert latex and containing 1‰ of sodium chloride (Brookfield RVT, No. 3 rotor; speed: 5 revolutions per minute); $\eta$=3 560 mPa·s.

Examples of Formulations

Example 4

Antistress Hair Care

| | Formula | |
|---|---|---|
| Phase A | Water | qs 100% |
| | Xanthan gum | 0.50% |
| Phase B | SEPICAP ™ MP | 3.00% |
| Phase C | Composition of Example 1 | 4.00% |
| Phase D | Butylene glycol | 5.00% |
| | LANOL ™ 99 | 5.00% |
| | SEPICIDE ™ HB | 0.30% |
| | SEPICIDE ™ CI | 0.20% |
| | Perfume | 0.20% |

Procedure

Disperse the xanthan gum in water with a deflocculating device. Then add SEPICAP™ MP, then the composition of Example 1; disperse it and then add the ingredients of Phase D.

Example 5

Restructuring Cream Mask for Stressed and Embrittled Hair

| | Formula | |
|---|---|---|
| Phase A | MONTANOV ™ 82 | 3.00% |
| | LANOL ™ P | 6.00% |
| | AMONYL ™ DM | 1.00% |
| | Isostearyl isononanoate | 5.00% |
| | Composition of Example 2 | 2.50% |
| Phase B | Water | qs 100% |
| Phase C | SEPICAP ™ MP | 3.00% |
| | SEPICIDE ™ HB | 0.30% |
| | SEPICIDE ™ CI | 0.20% |

Procedure

Melt Phase A at 75° C. Heat Phase B to 75° C. Emulsify A in B. At around 40° C., introduce the constituents of Phase C.

Example 6

Purifying Gel for the Face

| | Formula | |
|---|---|---|
| Phase A | MONTALINE ™ C 40 | 7.00% |
| | Pearlescent base 2078 | 5.00% |
| | Composition of Example 3 | 2.00% |
| Phase B | Water | qs 100% |

Example 7

Colouring Shampoo

| | Formula | |
|---|---|---|
| Phase A | MONTALINE ™ C 40 | 15.00% |
| | Disodium cocamphoacetate | 5.00% |
| | Cetrimonium chloride | 1.00% |
| | SEPIPERL ™ N | 3.00% |
| | Composition of Example 2 | 3.00% |
| Phase B | Colour | qs |
| | Water | qs 100% |

Example 8

Antimicrobial Soap for the Hands

| | Formula | |
|---|---|---|
| Phase A | MONTALINE ™ C 40 | 20.00% |
| | Glycerin | 5.00% |
| | Composition of Example 2 | 1.00% |
| Phase B | Water | qs 100% |

Example 9

Antiseptic Liquid Soap

| | Formula | |
|---|---|---|
| Phase A | MONTALINE ™ C 40 | 30.00% |
| | ORAMIX ™ NS 10 | 15.00% |
| | Chlorhexidine digluconate (at 20%) | 5.00% |
| | Composition of Example 1 | 2.00% |
| Phase B | Water | qs 100% |

The definitions of the commercial products used in the examples are the following:

SEPICIDE™ HB is a preserving mixture comprising phenoxy-ethanol, methylparaben, ethylparaben, propylparaben and butylparaben, marketed by the company SEPPIC.

SEPICIDE™ CI is imidazolidinylurea, marketed by the company SEPPIC.

ORAMIX™ NS 10: decyl glucoside marketed by SEPPIC.

MONTALINE™ C 40: (cocoammoniumcarbamoyl chloride) marketed by SEPPIC.

SEPIPERL™ N: (cocoyl glucoside/cocoyl alcohol) marketed by SEPPIC.

MONTANOV™ 82: (cocoyl glucoside/cetearyl alcohol) marketed by SEPPIC.

AMONYL™ DM: (quaternium 82) marketed by SEPPIC.

SEPICAP™ MP: (sodium cocoyl amino acids/potassium dimethicone copolyol panthenyl phosphate) marketed by SEPPIC.

LANOL™ P: (glycol palmitate) marketed by SEPPIC.

LANOL™ 99: (isononyl isononanoate) marketed by SEPPIC.

The invention claimed is:

1. A self reversible inverted latex comprising;
    an oily phase;
    an aqueous phase;
    at least one water-in-oil emulsifying agent; and
    at least one oil-in-water emulsifying agent comprising 25% to 70% by weight of a crosslinked cationic copolymer,
    wherein the crosslinked cationic copolymer is formed by inverse emulsion polymerization, and the crosslinked cationic compolymer comprises:
    from about 55% to about 95% of the monomeric units being acrylamide;
    from about 5% to about 35% of the monomeric units being at least one cationic monomer;
    from about 0.1% to about 5% of the monomeric units being at least one nonionic surfactant monomer of the formula (I):

$$A\text{-}C(=O)\text{-}O\text{-}[(CH_2\text{-}CH(R_1)\text{-}O]_n\text{-}R \qquad (I),$$

wherein:
    (i) n is from 1 to 10,
    (ii) A is a vinyl radical,
    (iii) $R_1$ comprises at least one component selected from the group consisting of a hydrogen atom, a methyl radical, and an ethyl radical, and
    (iv) R is a lauryl radical; and
    from about 0.005% to about 1% of a crosslinking agent, expressed relative to the monomers used,
    wherein said percentages are expressed in terms of monomeric units.

2. The self reversible inverted latex according to claim 1, wherein the acrylamide of the crosslinked cationic compolymer is an ethoxylated derivative thereof having a molecular weight in the range of from about 400 to about 1000.

3. The self reversible inverted latex according to claim 1, wherein the cationic monomer comprises at least one component selected from the group consisting of:
    a) 2, N,N,N-tetramethyl-2-[(1-oxo-2-propenyl)amino] propanammonium chloride (AMPTAC),
    b) 2, N,N-trimethyl-2-[(1-oxo-2-propenyl)amino] propanammonium chloride,
    c) N,N,N-trimethyl-3-[(1-oxo-2-propenyl)amino] propanammonium chloride (APTAC),
    d) diallyldimethylammonium chloride (DADMAC),
    e) N,N,N-trimethyl-2-[(1-oxo-2-propenyl)] ethanammonium chloride,
    f) N,N,N-trimethyl-2-[(1-oxo-2-methyl-2-propenyl)] ethanammonium chloride,
    g) N-[2-(dimethylamino)-1,1-dimethyl]acrylamide, N-[2-(methylamino)-1,1-dimethylacrylamide,2-(dimethylamino) ethyl acrylate,
    h) 2-(dimethylamino)ethyl methacrylate, and
    i) N-[3-(dimethylamino)propyl]acrylamide.

* * * * *